(12) United States Patent
Arnold et al.

(10) Patent No.: US 7,468,351 B2
(45) Date of Patent: Dec. 23, 2008

(54) ERYTHROPOIETIN SOLUTION FORMULATION

(75) Inventors: Stefan Arnold, Schwetzingen (DE); Okke Franssen, Utrecht (NL); Albert Mekking, Woerden (NL)

(73) Assignee: Bioggnerix AG, Manheim (DE)

( * ) Notice: Subject to any disclaimer, the term of this patent is extended or adjusted under 35 U.S.C. 154(b) by 21 days.

(21) Appl. No.: 10/581,269

(22) PCT Filed: Dec. 1, 2004

(86) PCT No.: PCT/EP2004/013619

§ 371 (c)(1), (2), (4) Date: Jun. 1, 2006

(87) PCT Pub. No.: WO2005/053745

PCT Pub. Date: Jun. 16, 2005

(65) Prior Publication Data

US 2007/0128231 A1    Jun. 7, 2007

(30) Foreign Application Priority Data

Dec. 1, 2003    (EP)    ................... 03027460

(51) Int. Cl.
  *A61K 38/00*    (2006.01)
  *A61K 38/18*    (2006.01)
  *C07K 14/505*    (2006.01)

(52) U.S. Cl. .......................... 514/8; 530/397

(58) Field of Classification Search ................ None
See application file for complete search history.

(56) References Cited

U.S. PATENT DOCUMENTS

| 4,806,524 | A |   | 2/1989 | Kawaguchi et al. | ............ | 514/8 |
| 4,992,419 | A |   | 2/1991 | Woog et al. | ............ | 514/8 |
| 5,376,632 | A | * | 12/1994 | Konings et al. | ............ | 514/8 |
| 5,656,289 | A | * | 8/1997 | Cho et al. | ............ | 424/455 |
| 6,645,522 | B2 | * | 11/2003 | Naeff et al. | ............ | 424/450 |
| 6,979,442 | B1 | * | 12/2005 | Canning et al. | ............ | 424/85.1 |
| 2003/0148938 | A1 |   | 8/2003 | Sharma et al. | ............ | 514/12 |
| 2004/0022861 | A1 | * | 2/2004 | Williams et al. | ............ | 424/489 |

FOREIGN PATENT DOCUMENTS

| DE | 101 61 577 A1 | 7/2003 |
| EP | 0 456 153 A1 | 5/1991 |
| EP | 0 909 564 A1 | 4/1999 |
| JP | 59078124 A * | 5/1984 |

OTHER PUBLICATIONS

Espada et al. A New Method for Concentration of Erythropoietin from Human Urine. Biochemical Medicine vol. 3, pp. 475-484 (1970).*

* cited by examiner

*Primary Examiner*—Marianne P Allen
*Assistant Examiner*—Regina M DeBerry
(74) *Attorney, Agent, or Firm*—Chalin A. Smith; Smith Patent Consulting, LLC

(57) ABSTRACT

A stable pharmaceutical formulation of erythropoietin is disclosed which contains tris-(hydrox-ymethyl)-aminomethane as stabilizer, whereby the formulation does not contain amino acids or human serumalbumin.

13 Claims, 4 Drawing Sheets

ERYTHROPOIETIN SOLUTION FORMULATION

Figure 1:
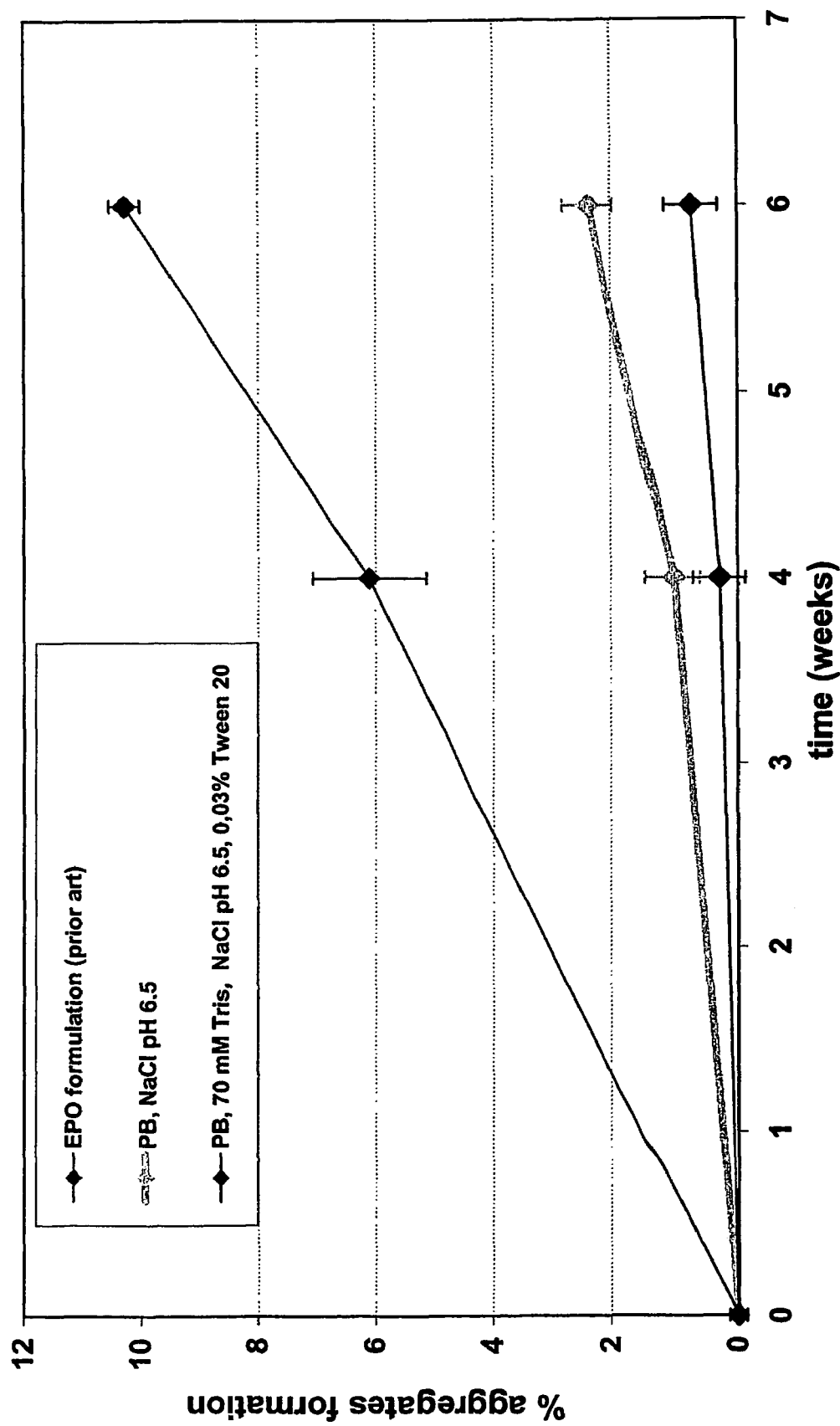

This application is a Rule 371 U.S. National Phase Filing of PCT/EPO04/013619, filed Dec. 1, 2004, which, in turn, claims priority to European Patent Application No. 03.027460.0 filed Dec. 1, 2003, the contents of which are incorporated by reference herein in their entirety.

Erythropoietin (hereinafter abbreviated as EPO) is a glycoprotein hormone which promotes the differentiation and proliferation of erythroid progenitor cells. Erythrocytes are present in the blood for certain periods of time. After a mean lifetime of about 120 days in humans the red blood cells are destroyed and removed from the body. On the other hand red blood cells are constantly supplied from the bone marrow so that the total number of erythrocytes is kept at a normal state. In particular patients suffering under renal diseases have not enough erythrocytes in the blood. Erythropoietin plays a central role in the formation of erythrocytes and it is therefore frequently used for the treatment of patients which are anemic. In particular patients with dialysis treatment receive permanently EPO.

The design of a drug for supplying the market with stable EPO preparations requires that chemical changes like hydrolysis, disulfide exchange reactions or physical changes like denaturation, aggregation or adsorption which do frequently occur with EPO formulations be suppressed as far as possible. Since EPO is a glycosylated polypeptide it has been frequently lyophilized for stabilization. The lyophilization increases, however, the manufacturing costs and the lyophilized drug has to be dissolved in order to prepare an aqueous solution immediately before applying to the patient. This is additional work for the physicians and it may cause problems when the solids are not easily and properly dissolved in the aqueous solution.

There have been several proposals for avoiding the stability problems. Products which were on the market contained human serumalbumin or purified gelatine which is generally used as stabilizer. Since it is, however, nearly impossible to exclude each and every risk of a possible viral or TSE (transmissible spongiform encephalopathies) related contamination those stabilizers have been substituted.

EP-A 909 564 of Chugai proposes an erythropoietin solution preparation containing an amino acid as a stabilizing agent. WO 00/61169 discloses pharmaceutical compositions of erythropoietin which are free of human serum blood products and which are stabilized with an amino acid and a sorbitan mono-9-octadecenoate poly(oxy-1,2-ethanediyl) derivative.

It has been noticed, however, that the known formulations still tend to form aggregates. Although it is not desired to be bound by a theory the formation of aggregates may be explained with the structure of EPO. The well-known sequence of EPO contains four cystein residues. There are two disulfide bridges between $cys^7$-$cys^{161}$ and $cys^{29}$-$cys^{33}$. It is assumed that due to oxidation-reduction processes in particular after a longer storage in an aqueous solution there may be rearrangements of the disulfide bridges which lead to aggregates which cannot be dissolved. This may result in undesired immunologic side reactions. Recently such side effects were reported for some patients with chronic renal anemia treated with erythropoietin (Eprex®, epoetin alfa). During the treatment these patients developed PRCA (pure red-cell aplasia), a severe immunological side effect leading to transfusion-dependent anemia (Casadevall 2002 "Antibodies against rHuEPO: native and recombinant." *Nephrol Dial Transplant* 17 Suppl 5: 42-7; Casadevall, Nataf et al. 2002 "Pure red-cell aplasia and antierythropoietin antibodies in patients treated with recombinant erythropoietin." *N Engl J Med* 346(7): 469-75). It is very likely that this adverse effect was caused by the pharmaceutical formulation of Eprex® (Schellekens 2003 "Relationship between biopharmaceutical immunogenicity of epoetin alfa and pure red cell aplasia." *Curr Med Res Opin* 19(5): 433-4).

It is therefore an object of the present invention to provide an erythropoietin solution formulation which is stable and wherein the formation of aggregates even at higher temperatures is substantially reduced or avoided completely.

The present invention provides therefore stable pharmaceutical formulations of erythropoietin as characterized in the claims.

The stable solution of erythropoietin comprises a pharmaceutical quantity of erythropoietin. The amount of erythropoietin ranges from about 1,000 IU/ml up to 40,000 IU/ml. Depending on the needs of the clinicians preferred concentrations are 2,000 IU/ml, 5,000 IU/ml and 10,000 IU/ml for intravenous (iv) and subcutanous (sc) injection as well. The term "erythropoietin" as used in the present invention includes those proteins which have the biological activity of human erythropoietin as well as erythropoietin analogues, erythropoietin isoforms, erythropoietin memetics, erythropoietin fragments, hybrid erythropoietin proteins or fusion proteins. The glycosylation pattern of erythropoietin has a strong effect and may therefore influence the units a certain amount of erythropoietin has.

The buffering agent to be used in the present solution is a sodium phosphate buffer. The buffer is used in order to maintain a pH value in the range of about 5.9 to about 6.8, preferably from 6.2 to 6.6 and most preferred between 6.4 to 6.5. The pH value may be adjusted with a corresponding base. In the phosphat buffer system of the present invention either in NaOH or phosphoric acid is used for this purpose. It is also possible to add KOH instead of NaOH. The amount of the buffering agent which is present in the pharmaceutical formulation ranges from about 5 mM to about 50 mM, preferably from about 10 mM to about 30 mM.

It has been surprisingly found that the erythropoietin solution can be stabilized by adding either NaCl or tris-(hydroxymethyl)-aminomethane (tris) or preferably both. The term "tris" covers all forms of this compound like the tris base or tris HCl. Solutions which are injected into the body of a patient have preferably a suitable osmolarity. This can be achieved by adding sodium chloride. In the course of the present invention it has been noticed that the addition of NaCl to the phosphate buffer reduces substantially the formation of aggregates. NaCl is added in an amount ranging from about 20 to about 150 mM whereby a range of 30 to 120 mM is preferred and most preferred is a range between 50 to 100 mM.

The stabilizing effect can also be obtained by adding tris-(hydroxymethyl)-aminomethane in an amount ranging from about 10 to about 150 mM, whereby a range from about 40 to about 100 mM is preferred. Tris-(hydroxymethyl)-aminomethane is well recognized as buffer system for pharmaceutical protein formulations in the prior art (e.g. WO 03/072060). Usually it is used in the pH range between 7 and 9. At pH values between pH 5.9 and pH 6.8 tris-(hydroxymethyl)-aminomethane shows no or just very low buffering properties. The surprising stabilizing effect of tris-(hydroxymethyl)-aminomethane is therefore not correlated with its buffering properties.

The stabilizing effect can be achieved by adding either natrium chloride or tris-(hydroxymethyl)-aminomethane.

The stabilizing effect is, however, substantially improved by adding both stabilizing agents, namely NaCl and tris together to the solution.

Furthermore the erythropoietin solution comprises preferably also a non-ionic surfactant, preferably polysorbate. Polysorbates are the polycondensation products of sorbitane esters and polyethylene glycol. The fatty acid residues of the sorbitane esters to be used according to the present invention are derived exclusively from plants, not from animals. This is important in order to improve the safety of the erythropoietin solution. Furthermore it is important that the peroxide content as determined according to Pharmacopoeia European (Ph Eur), section 2.5.5 is below 1.00 µMol/g, preferably below 0.5 µMol/g. This corresponds to a peroxide content between 0.01-1 µM, preferably below 0.5 µM as concentration of the final pharmaceutical composition. The polysorbates are commercially available, for example under tradenames Tween® 20 or Tween® 80, respectively.

It is to be noted that the erythropoietin solution formulation according to the present invention does not contain products derived from human blood, in particular human serumalbumin. Furthermore the formulation does not contain amino acids as stabilizer. Preferably the solution does also not contain urea. The formulation of the present invention does also not contain amino acids which are added to other formulations as stabilizer.

The erythropoietin solutions are used for injection. The formulations are therefore preferably injection solutions which are prepared for intravenous or subcutanous injection. Depending on the specific use the formulation may also contain usual additives of such injection solutions.

The invention is further illustrated by the following examples:

EXAMPLE 1

Preparation of Erythropoietin Solutions

EPO bulk drug product solutions were diluted to 100 µg/ml with various solutions to obtain the formulations as given in the following Tables 1 and 2.

Table 1 represents a formulation produced according to the prior art. This formulation contains as stabilizer glycine and the pH of this prior art formulation ranges from pH 6.6 to pH 7.2.

TABLE 1

| Formulation | EPO (µg/ml) | PB (mM) | NaCl (% w/v) | Glycine (mM) | Tween 80 (% w/v) | pH |
|---|---|---|---|---|---|---|
| prior art | 100 | 20 | 0.438 | 67 | 0.03 | 7.0 |

PB means phosphate buffer.

Furthermore formulations according to the present inventions were prepared. The formulations differ with regard to the content of NaCl and Tris. The formulations are given in the following Table 2.

TABLE 2

| Formulation | EPO (µg/ml) | PB (mM) | NaCl (mM) | Tris (mM) | Tween 20 (% w/v) | pH |
|---|---|---|---|---|---|---|
| A | 100 | 20 | 128 | 0 | 0.03 | 6.5 |
| B | 100 | 20 | 113 | 20 | 0.03 | 6.5 |

TABLE 2-continued

| Formulation | EPO (µg/ml) | PB (mM) | NaCl (mM) | Tris (mM) | Tween 20 (% w/v) | pH |
|---|---|---|---|---|---|---|
| C | 100 | 20 | 67 | 70 | 0.03 | 6.5 |
| D | 100 | 20 | 0 | 140 | 0.03 | 6.5 |

After preparation the solutions were filtered (PALL Gelman, Acrodisc, 0.2 µm, Supor membrane, nonpyrogenic, sterile) and filled (volume 1 ml) into 2 ml type I glass vials. No absorbtion of EPO on the filter was observed. Stoppered (using 13 mm flurotec siliconized butyl rubber stoppers, Daiichi) and capped vials were stored under ICH (ICH=International Conference on Harmonization of Technical Requirements of Pharmaceuticals for Human Use) conditions at 40 ±3° C./80% room humidity for up to 8 weeks.

In order to obtain comparable formulations Tween 20 and Tween 80, respectively, were used in the formulations. The Tween preparations as used had all a low initial peroxide content.

EXAMPLE 2

Determination of Aggregates

The degree of aggregation was measured with high pressure size exclusion chromatography (HP-SEC). By using the HP-SEC technology it is possible to determine exactly the amount of the EPO monomer. Dimers and multimers elute at different peaks. For the measurement a TSK G3000 SWXL, 5 µm, 300 ×7.8 mm was used. The mobile phase was a buffer comprising 150 mM NaCl, 10 mM $NaH_2PO_4 \times 2\ H_2O$, pH 7.2. The area under the peaks was calculated and the amount of EPO monomer was measured over a period of time up to 8 weeks. The samples were stored at 40° C. The results obtained are given in Table 3.

SD means standard deviation.

TABLE 3

A

| | weeks 40° C. | PB, NaCl pH 6.5 | SD |
|---|---|---|---|
| Aggregates Formation | 0 | 0 | 0.15 |
| | 4 | 1.05 | 0.42 |
| | 6 | 2.38 | 0.42 |
| | 8 | 2.27 | 0.53 |

B

| | weeks 40° C. | PB, 20 mM Tris, NaCl pH 6.5 0.03% Tween 20 | SD |
|---|---|---|---|
| Aggregates Formation | 0 | 0 | 0.15 |
| | 4 | 0.53 | 0.47 |
| | 6 | 1.35 | 0.41 |
| | 8 | 1.98 | 0.43 |

C

| | weeks 40° C. | PB, 70 mM Tris, NaCl pH 6.5 0.03% Tween 20 | SD |
|---|---|---|---|
| Aggregates Formation | 0 | 0 | 0.15 |
| | 4 | 0.31 | 0.43 |

TABLE 3-continued

|   | 6 | 0.77 | 0.43 |
|---|---|---|---|
|   | 8 | 2.14 | 0.61 |

D

| weeks 40° C. | PB, 140 mM Tris, NaCl pH 6.5 0.03% Tween 20 | SD |
|---|---|---|
| Aggregates Formation | 0 | 0 | 0.33 |
|  | 4 | 0.49 | 0.6 |
|  | 6 | 1.06 | 0.59 |
|  | 8 | 0.13 | 0.68 | prior art

| weeks 40° C. | EPO formulation (prior art) PB, Glycin, pH 7.0 0.03% Tween 80 | |
|---|---|---|
| Aggregates Formation | 0 | 0 | |
|  | 4 | 6.11 | 0.96 |
|  | 6 | 10.29 | 0.26 |
|  | 8 |  |  |

From Table 3 it can be seen that replacing the amino acid glycine by NaCl and/or Tris a significant reduction of the formation of aggregates was obtained. The results of experiment 3 are shown in FIG. 1-4. All experiments were performed in phosphate buffer (PB).

In FIG. 1 the formation of aggregates over time (up to six weeks) is shown. Most aggregates were found in a formulation wherein glycine was used as stabilizing factor (prior art). This was compared with formulations according to the present invention wherein either NaCl or 70 mM Tris and NaCl were present.

Figure 2:
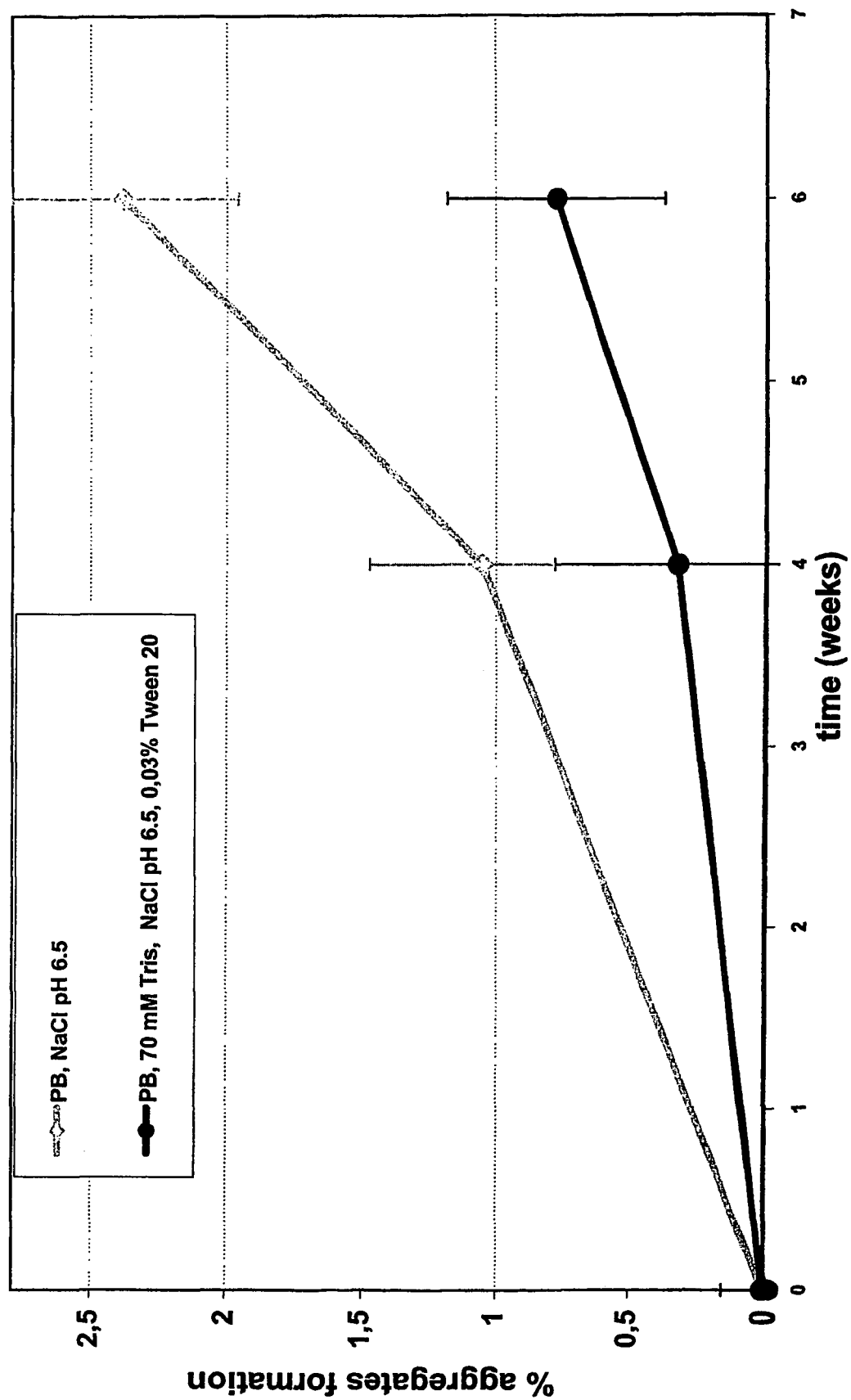

FIG. 2 shows in an enlarged scale the effect of adding 70 mM Tris and 0.03% Tween in addition to NaCl.

Figure 3:
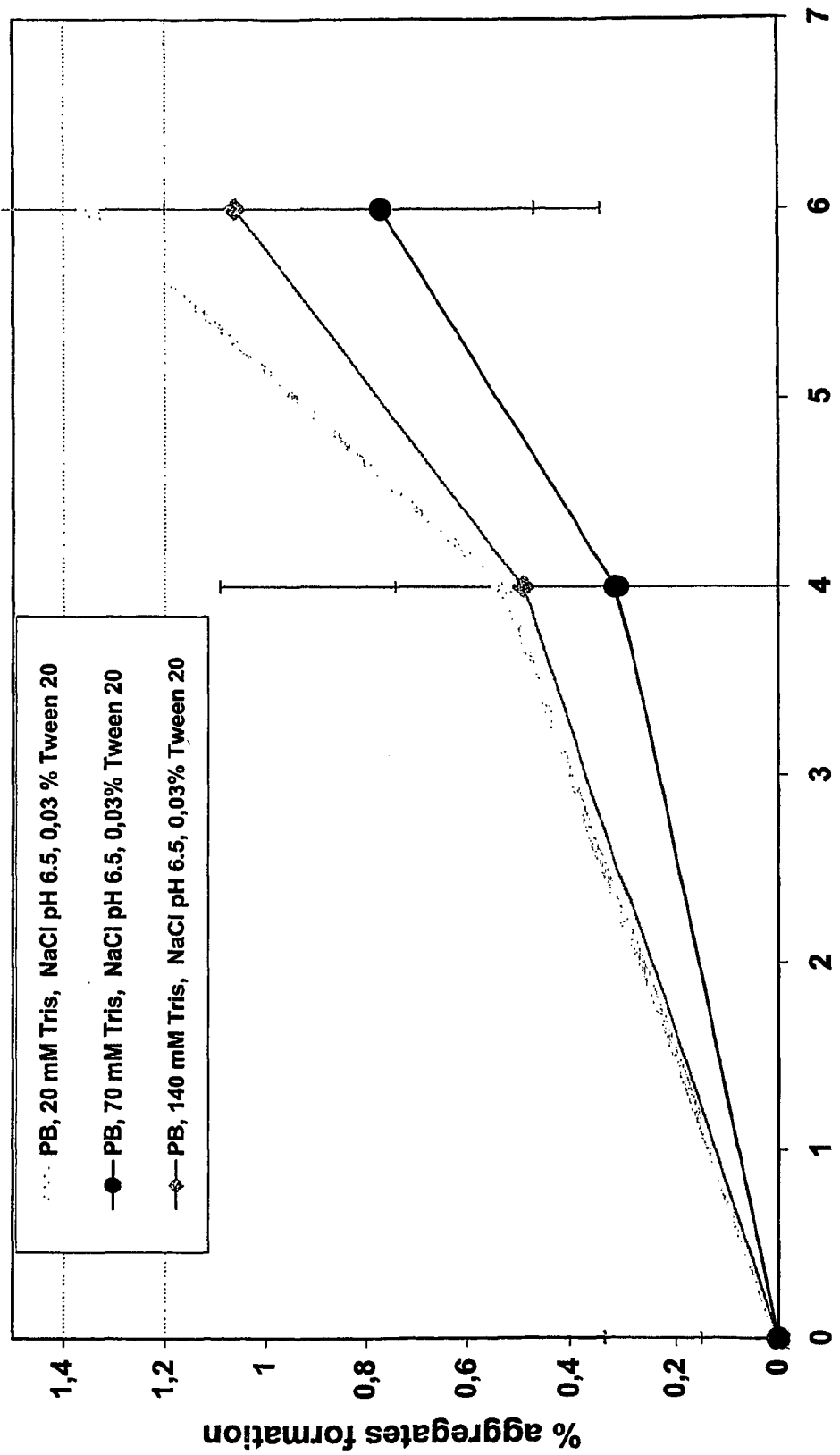

FIG. 3 shows the effect of the amount of Tris in formulations which contain also NaCl and Tween 20. It can be seen that good results can be obtained within a range between 20 mM Tris and 140 mM Tris whereby best results were obtained with about 70 mM Tris.

Figure 4:
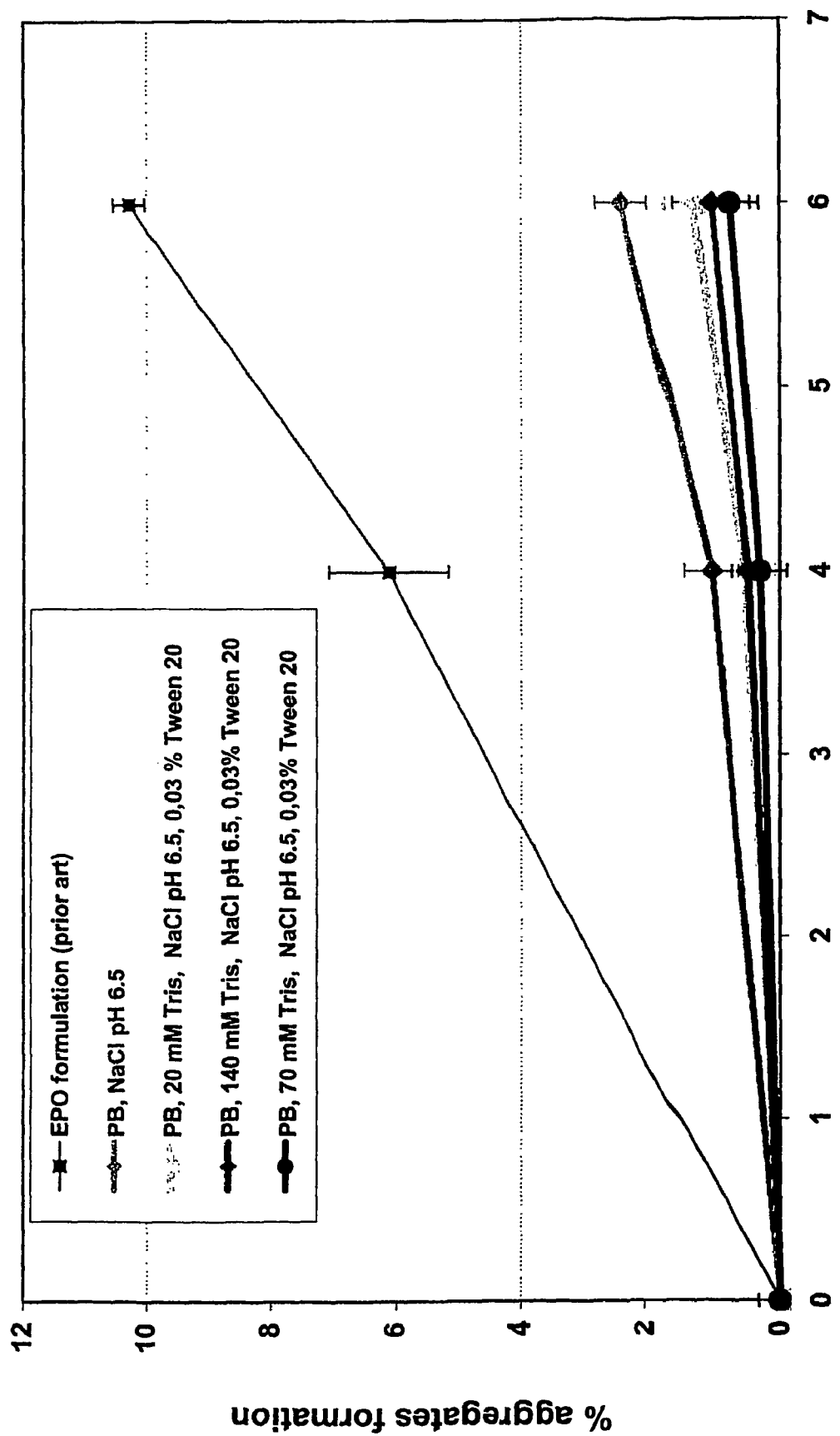

FIG. 4 shows a comparison between the formulation known from the prior art and formulations according to the invention. The lowest formation of aggregates was observed with about 70 mM Tris, NaCl, and 0.03% Tween 20 with a pH value of 6.5.

The invention claimed is:

1. A stable phosphate-buffered pharmaceutical formulation of erythropoietin containing tris-(hydroxymethyl)-aminomethane as stabilizer, whereby the formulation does not contain amino acids or human serum albumin, further wherein the pH of the formulation ranges from 5.9 to 6.8.

2. A stable pharmaceutical formulation of claim 1 comprising:
   a) as a pH buffering agent a sodium phosphate buffer,
   b) as stabilizer tris-(hydroxymethyl)-aminomethane in an amount of 10 to 200 mM, and
   c) a pharmaceutical quantity of erythropoietin.

3. The formulation of claim 2 which comprises NaCl in an amount of 20-150 mM.

4. The formulation according to claim 3 wherein the amount of NaCl ranges from 50 to 100 mM.

5. The formulation of claim 2 wherein the pH buffering agent has the formula $Na_xH_yPO_4$ wherein x is 1 or 2 and y is 1 or 2 and the sum of x and y is 3 whereby the pH buffering agent is present in the pharmaceutical formulation in a range of 5 mM to 50 mM.

6. The formulation of claim 1 which is an aqueous formulation.

7. The formulation of claim 1 wherein the tris-(hydroxymethyl)-aminomethane is present in an amount of 20 to 100 mM.

8. The formulation of claim 1 which contains also a non-ionic detergent in an amount ranging from 0.005 to 0.1 % w/v.

9. The formulation of claim 8 wherein the non-ionic detergent is a polysorbate.

10. The formulation according to claim 9 wherein the polysorbate is not produced from materials derived from animals and wherein the content of peroxide is lower than 1.00 µmol/g.

11. The formulation of claim 9, wherein the non-ionic detergent is Tween 20 or Tween 80.

12. The formulation according to claim 1 which comprises further ethylenediaminetetraacetic acid in an amount of 0.1 to 0.5 mM.

13. The formulation of claim 1, wherein the pH ranges from 6.2 to 6.6.

* * * * *